United States Patent [19]
Glynn

[11] Patent Number: 5,774,865
[45] Date of Patent: Jun. 30, 1998

[54] PATIENT COMPLIANCE AND MONITORING SYSTEM FOR MULTIPLE REGIMENS USING A MOVABLE BAR CODE READER

[75] Inventor: Kenneth P. Glynn, Raritan Township, N.J.

[73] Assignee: Ideal Ideas, Inc., Flemington, N.J.

[21] Appl. No.: 635,013

[22] Filed: Apr. 19, 1996

[51] Int. Cl.$^6$ .................................................. G06F 17/60
[52] U.S. Cl. ................................ 705/2; 705/3; 600/300; 177/25.19
[58] Field of Search .......................... 705/2, 3; 600/300; 177/25.19

[56] References Cited

U.S. PATENT DOCUMENTS

| | | | |
|---|---|---|---|
| 4,899,839 | 2/1990 | Dessertine et al. | 177/25.19 |
| 5,014,798 | 5/1991 | Glynn | 177/25.19 |
| 5,016,172 | 5/1991 | Dessertine | 600/300 |
| 5,582,323 | 12/1996 | Kurtenbach | 221/2 |
| 5,612,869 | 3/1997 | Lentzl et al. | 705/3 |
| 5,626,144 | 5/1997 | Tacklind et al. | 600/538 |

*Primary Examiner*—Tariq R. Hafiz
*Assistant Examiner*—Jagdish Patel
*Attorney, Agent, or Firm*—Kenneth P. Glynn, Esq.

[57] ABSTRACT

The patient compliance and monitoring device utilizes a tray with a base for holding medicine containers such as bottles. Inside the base attached to the tray is a weight scale connected to a computer. Also connected to the computer are an alphanumeric keyboard and an LCD monitor which attached to the base. The computer entails a microprocessor connected to ROM and RAM and encoded with instruction sets to determine the dosage taken by a user as well as the date and time taken. The medicine containers are detected, preferably, by a bar code reader inside the base scanning bar code labels attached to the bottom of the medicine containers.

20 Claims, 3 Drawing Sheets

PATIENT COMPLIANCE AND MONITORING SYSTEM FOR MULTIPLE REGIMENS USING A MOVABLE BAR CODE READER

BACKGROUND OF THE INVENTION

1. Field of the Invention

The present invention is directed to a patient compliance and monitoring system for multiple regimens. More particularly, the device monitors medicine intake by identifying the particular medicine bottle taken from the device and the dosage taken from the particular medicine bottle.

2. Information Disclosure Statement

The use of computers with mechanical devices to monitor a patient's usage of medicine is continuously evolving.

U.S. Pat. No. 4,899,839 issued to Dessertine et al. is directed to a method of monitoring a patient's medicine compliance. It involves weighing a container of medicine to determine a starting weight on a scale which is connected to a computer with a display unit and storing the starting weight in the computer followed by a reweighing of the container of medicine after a prescribed dosage is consumed to determine a second weight. The computer then determines the difference between the starting weight and the second weight to store a dosage unit weight. The computer is programmed to calculate compliance required weight of the container for each dosage administered for the prescription period of the medicine. The container of medicine is reweighed from time to time on the scale to compare actual weight with compliance required weight to determine compliance and the computer visually displays the compliance results on the display unit to permit compliance monitoring.

U.S. Pat. No. 5,014,798 issued to Glynn is directed to a cap for a medicine bottle for monitoring a patient's medicine compliance. It involves weighing a container of medicine with cap which includes scale means located therein which is connected to a computer chip with a display unit also located in or on the cap. The chip may store the starting weight or tare weight, plus total weight and when the container or medicine is picked up by the cap at any time, actual weight is fed to the chip. The computer chip may then determine the difference between the starting weight and/or display actual amount of medicine remaining or consumed. The container of medicine is reweighed from time to time with the cap, and the chip may compare actual weight to determine compliance and the cap may visually display the compliance results on the display unit to inform the patient.

U.S. Pat. No. 5,016,172 issued to Dessertine is directed to a method of monitoring a patient's medicine compliance by the number of cap openings, by dispensing count or by weight information obtained by the automatic compliance monitoring device, for each dosage administration for the prescription period. The automatic compliance monitoring device is periodically or randomly connected to a computer to compare actual usage with compliance required to determine compliance results on the display unit to permit compliance monitoring on a monitor at a remote location.

Notwithstanding the prior art there is no suggestion or teaching for a patient compliance and monitoring system or device for multiple medicine regimens.

SUMMARY OF THE INVENTION

The present invention concerns a patient compliance and monitoring device for multiple medicine regimens. The device has a tray mounted on a base. The tray is for holding multiple medicine containers. The base houses a computer connected to a weight scale, a reader, a positioner, input means, output means and a power supply. Preferably, the computer is a microprocessor with interconnected RAM and ROM and the reader is a cylindrical or pen style bar code reader for scanning bar code labels on the medicine containers. The input means may be an alphanumeric keyboard and the output means may be an LCD monitor. The positioner is preferably a servomotor with a gear drive for moving the bar code reader in a two dimensional arc pattern.

Alternatively, the reader may be a magnetic detector for reading magnetic signatures on disks attached to the medicine containers. Also, the reader may be a transceiver for reading the reflective signature of a medicine container subjected to a laser light.

The present invention may be modified to incorporate separate bar code readers under each partitioned section of the tray. In this manner there may be one bar code reader for each possible medicine container.

BRIEF DESCRIPTION OF THE DRAWINGS

The present invention should be more fully understood when the specification herein is taken in conjunction with the drawings appended thereto, wherein.

DETAILED DESCRIPTION OF THE PRESENT INVENTION

The present invention involves a patient compliance and monitoring system for multiple medicine regimens. More specifically, the system allows random placement of medicine containers, whether the medicine is in pill form or liquid form, to be placed in a medicine tray which is connected to a computer. The computer stores usage data, such as the dates, times and dosages taken, into memory and allows a user to recall the usage data at a later time or the usage data can be downloaded into another computer for more extensive patient compliance analysis.

Figure 1:
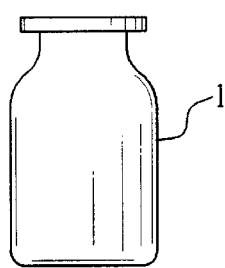
FIG. 1 is a side view of a typical medicine container.
Figure 2:
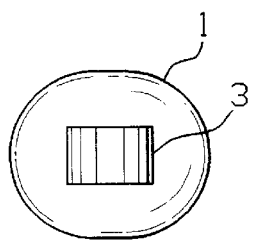
FIG. 2 is a bottom view of a medicine container with a bar code label.

Referring now to FIG. 1 there is shown a medicine container 1 which is typically a glass or plastic bottle type container for holding pills or liquid medicine. FIG. 2 shows the bottom of the medicine container 1 with a bar code label 3. Generating bar code labels like the one shown in FIG. 2 is well taught by the prior art.

Figure 3:
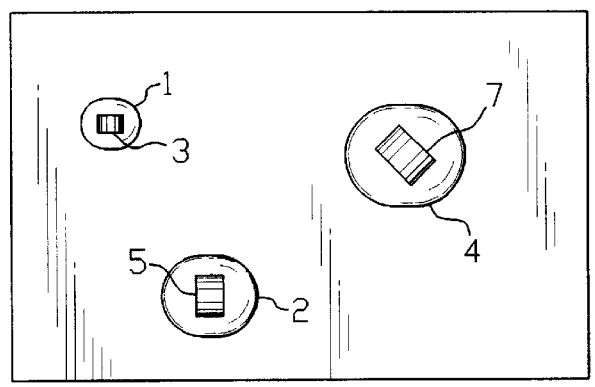
FIG. 3 is a bottom view of a medicine tray with medicine bottle bottoms having bar code labels.

Shown in FIG. 3 is the bottom of a medicine tray 9 of the present invention with three medicine bottles 1, 2 and 4 randomly located on the medicine tray 9. The medicine bottles 1, 2 and 4 have bar code labels 3, 5 and 7 secured to their bottoms. The bottom or support platform of the medicine tray preferably has a transparent or translucent quality so as to permit light, such as laser generated light, to be transmitted by a bar code scanner to penetrate the bottom of the tray and detect the bar code label pattern.

Figure 4A:
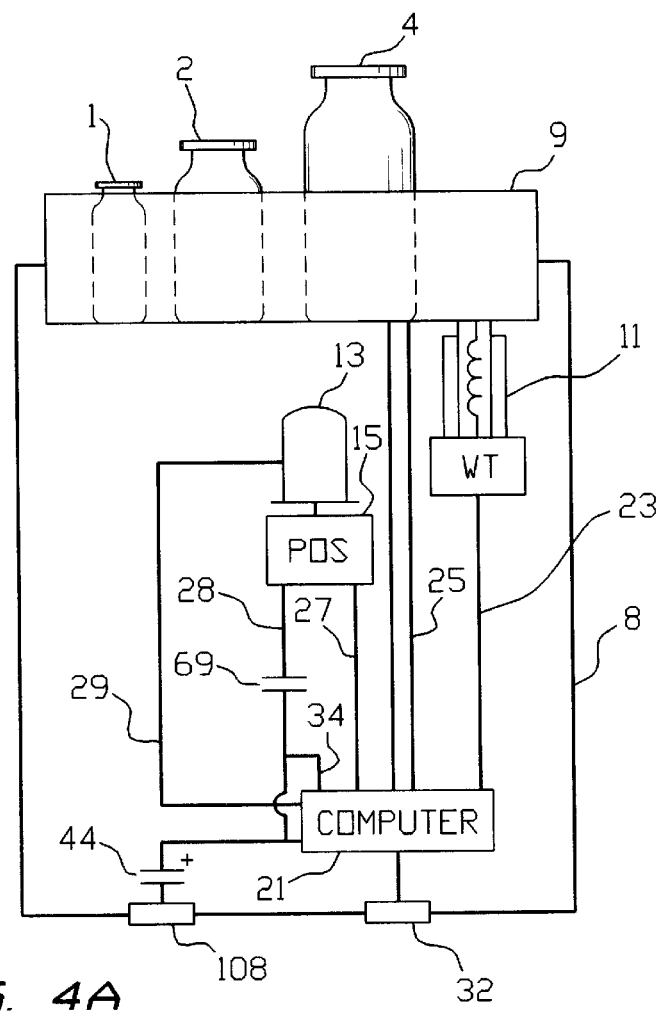
FIG. 4A is a partially cut side view of a patient compliance and monitoring device.

A partially cut side view of the present invention is depicted in FIG. 4A. The medicine tray 9 is slidably attached to a base 8. Vertical weight displacement of the medicine tray 9 is sensed by a weight scale 11 which is electrically connected via conductor 23 to a computer 21. Preferably, the weight scale 11 is a spring based weight sensing device with an electrical transducer for generating an analog electrical signal representing the weight sensed. Also, the weight scale 11, preferably, includes an analog to digital converter which converts the analog weight measurement to digital or binary signals to the computer 21. Power supply 44 is connected to the computer 21 and through switch 69 to a positioner 15 via conductor 28. the computer 21 is connected to the switch 69 via conductor 34 to provide a control signal to permit switch 69 to close, thereby activating the positioner 15, or to open, thereby deactivating the positioner 15. Power supply 44 is preferably a rectified alternating circuit wherein the alternating current power may be fed through connector 108. Alternatively, power supply 44 may be an electrochemical power supply such as batteries which may be used alone or in conjunction as a backup with a rectified alternating current supply.

The bar code reader 13 is fixedly attached to the positioner 15 labelled "pos" and electrically connected to the computer 21 via cable or conductor 29. The bar code reader 13 can be of a cylindrical pen style taught by the prior art. The bar code reader 13 is fixedly attached to the positioner 15 so as to be moved in a two dimensional arc pattern, a dome pattern or a hemispherical pattern so as to permit the bar code reader 13 to scan the entire bottom of the medicine tray 9 within the bar code reader's 13 periphery scanning range.

Preferably the positioner 15 is a servo motor which is controlled by the computer 21 via an electrical connection 27. The positioner 15 may generate the two dimensional arc pattern by means of an integral gear drive or pulley system.

Figure 4B:
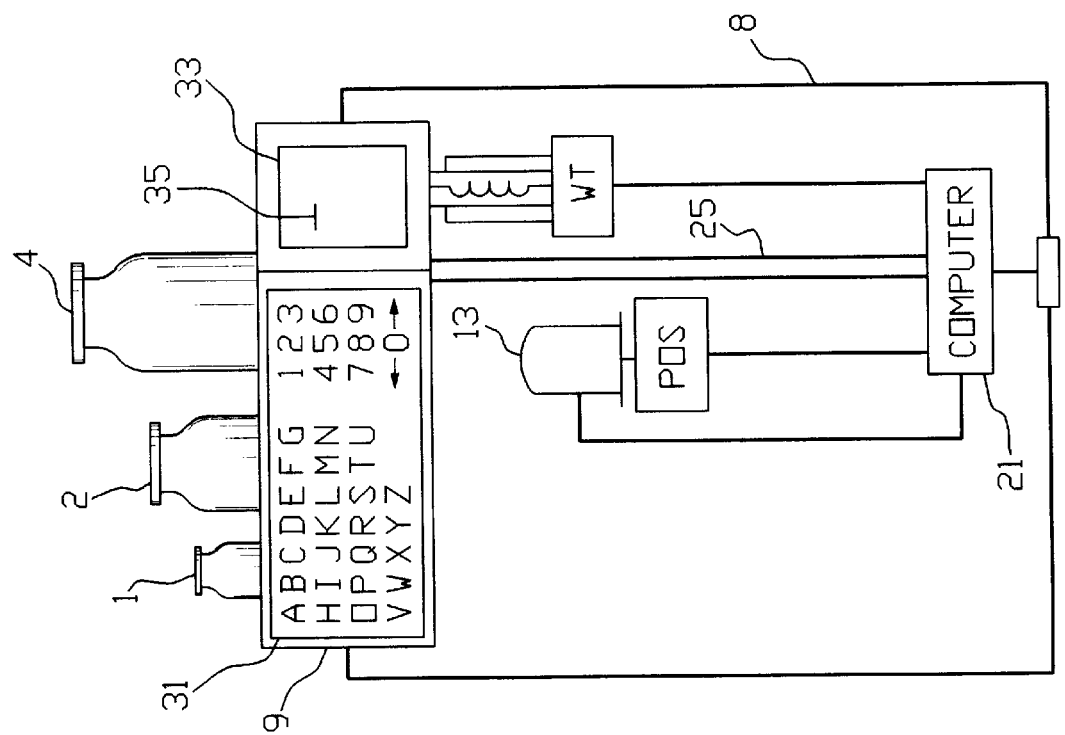
FIG. 4B is the partially cut side view of FIG. 4A with an alpha numeric keyboard and display attached to the base.

FIG. 4B, in addition to having the same parts as in FIG. 4A with similar reference numbers, shows an input means 31 and output means 33 electrically connected to the computer via conductor cable 25. Preferably, the input means 31 is an alphanumeric keyboard and the output means is a Liquid Crystal Display (LCD). Preferably, both the input means 31 and output means 33 are attached to the base 8. Alternatively, the input means may simply be cursor 35 positioning keys for manipulating a menu based program encoded in the computer 21, or a microphone for voice activated menu type commands. Likewise, the output means 33 can alternatively be a light emitting diode display.

Figure 5:
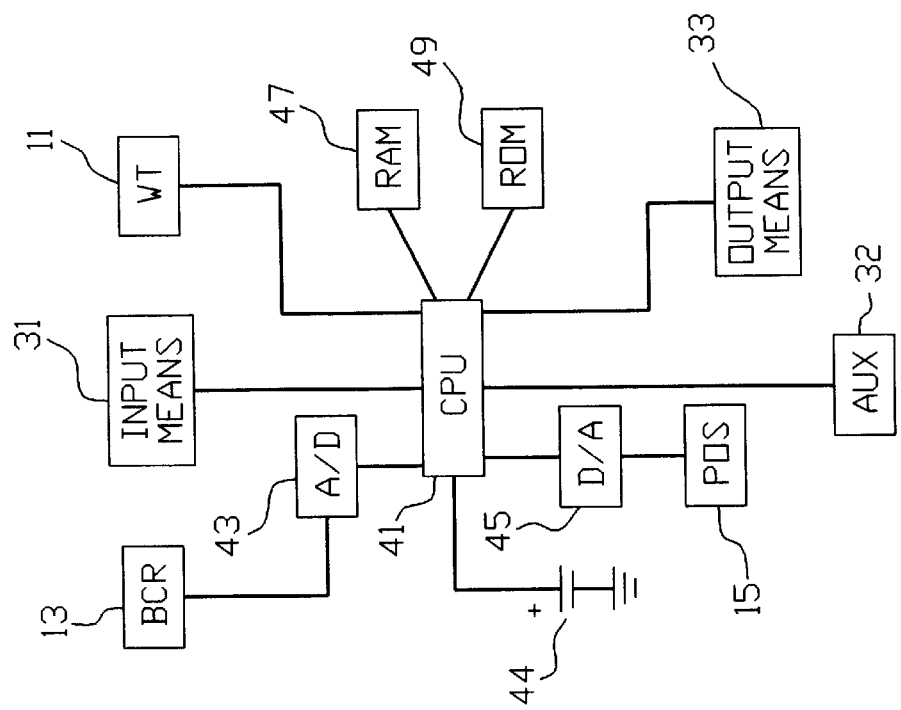
FIG. 5 is a block schematic of the computer of FIGS. 4A and 4B showing the electrical connections and logic interrelationships.

Referring now to FIG. 5, there is a block schematic of the computer 21 in FIGS. 4A and 4B, showing the electrical connections and interrelationships between the components. Like components from the prior figures are similarly numbered. The central processing unit (CPU) 41 may receive electrical input signals from the bar code reader 13, the input means 31, and the weight scale 11, and may send electrical output signals to the positioner 15 and output means 33. Also shown are analog to digital (A/D) 43 and digital to analog (D/A) 45 converters for inputs from the bar code reader 13 to the CPU 41 and outputs to the positioner 15 from the CPU 41. Alternatively, these A/D and D/A converters may be integral components of the bar code reader 13 and positioner 15, rather than separate components as shown. The power supply 44 may be battery or electrochemical supplied power (not shown) or rectified alternating current power supply typically provided by utility companies. Circuits for rectifying an alternating power supply into a power supply with direct current characteristics is well known in the art.

The central processing unit (CPU) 41 may be a microprocessor electrically connected to a read only memory (ROM) component 49 and a random access memory (RAM) component 47. The ROM is an array of permanently encoded memory cells containing the instruction sets, programming or algorithms necessary for the CPU 41 to interpret the inputs from the bar code reader 13, input means 31 and weight scale 11, properly process these inputs, and transmit appropriate electrical signals to either the positioner 15 or the output means 33. Alternatively, the CPU 41 may be a programmable logic controller with permanent and volatile memory storage capabilities similar to the ROM and RAM preferred. Programmable logic controllers are well known in the art. The programmable logic controller is a general application computer with preset input and output connection points. The programmable logic controller is encoded with instruction sets unique to the particular manufacturer of the programmable logic controller.

Also shown is an optional auxiliary connector 32 for connecting the CPU 41 to an external computer (not shown) and down loading any data stored in the RAM 47 to the external computer. The auxiliary connector 32 may accommodate a direct CPU 41 to the external computer hook up or it may accommodate a modem hookup for transmission via the phone lines to an external computer at a doctor's office or a hospital.

In a preferred embodiment of the present invention, the computer may be programmed to scan the tray 9 each time a change in weight is sensed by the weight scale, which would occur each time a medicine container is placed onto the tray 9 or retrieved from the tray 9. A user or patient may then initialize the computer with the correct date and time and identity of any and all medicine containers put on the medicine tray 9. Identity of medicine containers may be initialized by individually placing bar code labelled containers individually on the medicine tray 9 for scanning by the bar code reader 13. The computer 21 may be programmed to prompt via the output means 33 for identity information whenever a bar code label not stored in memory is scanned. The user may then via the input means 31 by way of menu options or direct keyboard inputs identify the medicine container by its common name, chemical name or some other alphanumeric identity. The computer 21 may then prompt for total medicine weight or dosage weight in the medicine container, if known. If not known, the user or patient may be instructed by the computer 21 to remove one dosage count from the medicine container, whether pill or liquid form, so that the computer 21 may determine and store the weight a single dosage by the difference in weight of the container before and after the single dosage count is removed.

The computer 21 may be programmed to store into the RAM 47, the date, time and dosage for any particular medicine that is retrieved from the medicine tray 9. When any medicine container is removed from the tray 9, the change in weight sensed by the weight scale would prompt a signal change to the computer 21. The computer 21 may in turn direct the bar code reader 13 to scan the bottom of the tray 9 to detect which bar code label is missing thereby indicating which medicine container or bottle was taken. When the medicine container is returned to the tray 9, the change in weight may prompt the computer to scan the bottom of the tray 9 and note which medicine container was returned. The computer 21 can determine from weight readings by the weight scale 11, before the container was taken and after the container is returned, how much medicine was withdrawn from the container.

The CPU 41 may be encoded to organize the usage data such as date, time and dosage taken as a two dimensional memory array having multiple rows and three columns for storing said date, time and dosage taken. The usage data can be stored as a last in first out (LIFO) memory stack whereby the most recent usage data is currently displayed on the output means 33, or as a first in first out (FIFO) memory stack whereby the first usage data stored is currently displayed in the output means 33. The user may scroll through the LIFO or FIFO memory stack to view on the output means 33 all usage data stored on the RAM 47.

The CPU 41 may also be programmed to store a usage or prescribed medicine regimen and perform compliance analysis by comparing actual usage to usage to the prescribed medicine regimen. The CPU 41 may generate an index based on hourly, daily, weekly or monthly deviations by the patient from the prescribed medicine regimen. The usage data may be accessed by the patient or a doctor through the input means 31 and output means 33, or the usage data may be transmitted via the auxiliary connector 32 through a modem over telephone communication systems to a doctor, pharmacy or hospital. As an option (not shown) the output means 33 may also include an audio transducer such as a speaker for providing audio signals reminding the user that medicine intake is required or that medicine intake is past due. The audio signals may be simple beeps or voice synthesized verbal commands.

Figure 6:
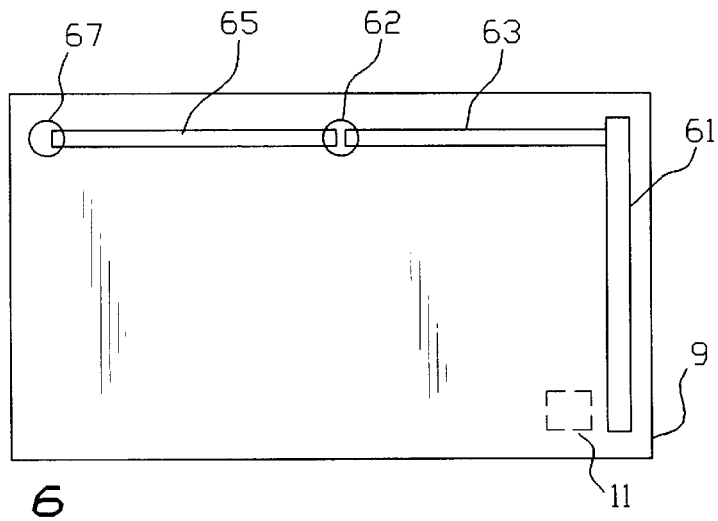
FIG. 6 is a top view of an alternative embodiment of a patient compliance and monitoring system.

Shown in FIG. 6 is a top view of an alternative embodiment to that in FIGS. 4A and 4B. Like parts in the prior figures are like numbered. A linear bar code reader 61 is a liner scanner about as wide as the medicine tray 9. The linear bar code reader 61 is swept across the bottom of the tray 9 by rotating means 67 turning a quarter circle clockwise to scan and a quarter circle counter clockwise to return to the starting position. As the rotating means 67 turns, two linkages 63 and 65 fold together by turning at rotatable connection point 62. Linkage 65 is fixedly connected to the motor drive 67, while linkage 63 is rotatably connected to bar code reader 61. Preferably the rotating means 67 is an electrically reversible direct current motor. Alternatively, the rotating means 67 may be a direct current motor with a gear drive system having opposing intermittent gears for achieving the clockwise and counter clockwise quarter turn sequences.

Figure 7:
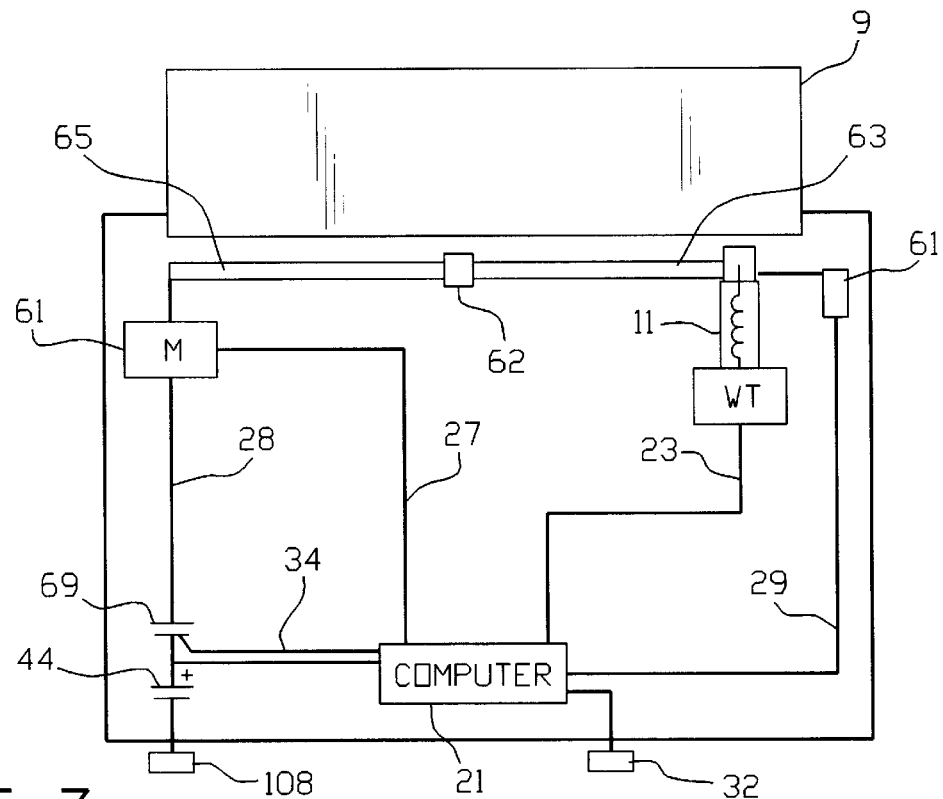
FIG. 7 is a partially cut side view of the alternative embodiment of FIG. 6.

Shown in FIG. 7 is a partially cut side view of the alternative embodiment of FIG. 6. The computer 21 receives electrical input from the weight scale 11 via conductor cable 23 and linear bar code reader 61 via conductor cable 29, and transmits an electrical control signal to switch 69 via conductor cable 34. Switch 69 is controlled by the computer 21 to permit current flow to the rotating means 67 from the power source 44. The power source 44 is also the power supply to the computer 21 and is preferably an alternating current power supply that is rectified to direct current characteristics. Input means 31 and output means 33 (not shown in FIGS. 6 or 7) are similar to those discussed for FIGS. 4A through 5.

In this alternative embodiment, the linear bar code reader 61 may be moved under the tray 9 only once to scan all the medicine containers.

The RAM 47 may be sectioned to allow the CPU 41 to sequentially store several bar codes in parallel or simultaneously. For example, if three bar codes are similarly positioned, the CPU 41 will sequentially store the first bar of each bar code, then sequentially store the second bar of each bar code, and then store the third bar of each bar code, and so on, until each bar code is entirely stored. This method of reading several bar codes simultaneously is in contrast to the preferred embodiment, where the bar code reader 13 is continuously moved by the positioner 15 in a predetermined pattern to read each bar code label one at a time or in series.

In a further alternative embodiment, the bar code reader 13 can be a hand held pen type connected to the computer 21 via a flexible electrical cord. In this embodiment the user may manually scan a bar code label, attached to the side of a container, before the container is retrieved from the tray and after the container is returned to the tray 9. The weight scale 11 would still function as discussed, providing the computer 21 with weights of the container before removal from the tray 9 and after return of the container to the tray 9.

In yet a further alternative embodiment, the bar code reader 13 can be substituted with a laser transceiver, i.e. a transmitter and receiver, and the computer 21 can be programmed to recognize each medicine container's unique light refractive and reflective signature when subjected to light such as from a laser source. Hence the bar code label 3 may be eliminated. It is well known in the prior art that different items of glass or plastic, whether in plate or container form, are not homogenous and therefore exhibit different reflective and refractive characteristics when subjected to light sources such as lasers.

Figure 8:
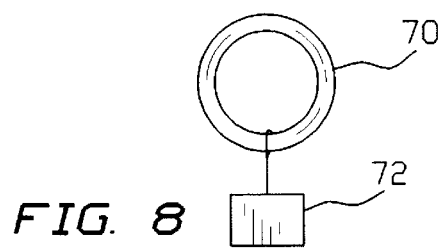
FIG. 8 is a side view of a stretchable band with a magnetic media.

Shown in FIG. 8 is yet a further alternative embodiment, wherein the bar code label can be replaced with a stretchable band 70 secured to a magnetic media 72, preferably a disk, encoded with a magnetic signature. The stretchable band 70 may be wrapped around the medicine container with the magnetic media 72 positioned under the medicine container 1.

Likewise, the bar code reader 13 may be replaced with a magnetic reader for detecting the magnetic signature of each magnetic media 72 under a medicine container on the tray 9.

Obviously, numerous modifications and variations of the present invention are possible in light of the above teachings. For example, rather than having a bar code reader that is positioned, such as the pen or linear style as shown in FIGS. 3 to 6, the tray 9 can have predetermined, partitioned sections with separate, bar code scanners positioned under each partitioned section. It is therefore understood that within the scope of the appended claims, the invention may be practiced otherwise than as specifically described herein.

What is claimed is:

1. A patient compliance and monitoring device for multiple medicine regimens comprising:
   (a) a medicine tray for holding a plurality of medicine containers having a bottom, said medicine tray having a reciprocally attached base;
   (b) a computer inside said base, said computer including:
      1) a central processing unit;
      2) random access memory electrically connected to said central processing unit; and,
      3) read only memory electrically connected to said central processing unit, said read only memory being encoded with instruction sets;
   c) a positioner inside said base, said positioner being electrically connected to said computer, said positioner being pivotable in a partially hemispherical pattern;
   d) a scanner inside said base, said scanner being electrically connected to said computer;

e) a weight scale inside said base, said weight scale being electrically connected to said computer, said weight scale being attached to said medicine tray and said base so as to allow said medicine tray to reciprocally slide relative to said base;

f) input means electrically connected to said computer and fixedly attached to said base for allowing a user to initialize said computer and recall usage data from said computer;

g) output means electrically connected to said computer and mounted to exterior of said base for displaying usage data; and, h) a switch inside said base, said switch being electrically connected to said computer, said positioner and a power supply.

2. The device of claim 1, wherein said central processing unit is a microprocessor.

3. The device of claim 2, wherein said scanner is a bar code reader.

4. The device in claim 3, wherein said input means is an alphanumeric key board.

5. The device of claim 4, wherein said output means is an liquid crystal display.

6. The device of claim 5, wherein said weight scale is a spring activated, weight sensing device with an electrical transducer.

7. The device of claim 6, wherein said positioner is a servomotor with a gear drive train.

8. The device of claim 2 wherein said scanner is a magnetic reader for detecting magnetic signatures on magnetic media attached to a medicine container on said tray.

9. The device in claim 8, wherein said input means is an alpha numeric key board.

10. The device of claim 9, wherein said output means is an liquid crystal display.

11. The device of claim 10, wherein said weight scale is a spring activated, weight sensing device with an electrical transducer.

12. The device of claim 11, wherein said positioner is a servomotor with a gear drive train.

13. The device of claim 12, wherein said switch is a one way switch for permitting current flow from said power supply to a rotating means for rotating a linear bar code reader, said one way switch being controlled by said computer.

14. A patient compliance and monitoring device for multiple medicine regimens comprising:

(a) a medicine tray for holding a plurality of medicine containers having a bottom for permitting propagation of light waves, said medicine tray having a reciprocally attached base;

(b) a computer inside base, said computer including:
1) a central processing unit;
2) random access memory electrically connected to said central processing unit; and,
3) read only memory electrically connected to said central processing unit, said read only memory being encoded with instruction sets;

c) rotating means electrically connected to said computer;

d) a first linkage having a first end and a second end, said first end being attached to said rotating means;

e) a second linkage having a first end and a second end, said first end of said second linkage being rotatably connected to said second end of said first linkage;

d) a linear bar code reader inside said base, said linear bar code reader being electrically connected to said computer and rotatably coupled to said second end of said second linkage;

e) a weight scale inside said base, said weight scale being electrically connected to said computer, said weight scale being attached to said medicine tray and said base so as to allow said medicine tray to reciprocally slide relative to said base;

f) input means electrically connected to said computer and fixedly attached to said base for allowing a user to initialize said computer and recall usage data from said computer;

g) output means electrically connected to said computer and fixedly attached to said base for displaying usage data; and, h) a switch inside said base, said switch being electrically connected to said computer, said positioner and a power supply.

15. The device of claim 14, wherein said central processing unit is a microprocessor.

16. The device of claim 15, wherein said rotating means is a direct current motor, said direct current motor being rotatably reversible.

17. The device of claim 16, wherein said input means is an alpha numeric key board.

18. The device of claim 17, wherein said output means is an liquid crystal display.

19. The device of claim 18, wherein said weight scale is a spring activated, weight sensing device with an electrical transducer.

20. The device of claim 19, wherein said switch is a one way switch for permitting current flow from said power supply to said rotating means, said one way switch being controlled by said computer.

* * * * *